United States Patent [19]

Nagamine et al.

[11] Patent Number: 4,650,326
[45] Date of Patent: Mar. 17, 1987

[54] APPARATUS FOR INSPECTING BOTTLES

[75] Inventors: Keiji Nagamine, Suita; Ichirou Handa, Ibaragi, both of Japan

[73] Assignee: Mitsubishi Denki Kabushiki Kaisha, Tokyo, Japan

[21] Appl. No.: 622,169

[22] Filed: Jun. 19, 1984

[30] Foreign Application Priority Data

Jun. 21, 1983 [JP] Japan ................................ 58-113064

[51] Int. Cl.[4] ............................................. G01N 21/90
[52] U.S. Cl. .................................... 356/240; 209/526; 250/223 B
[58] Field of Search ............................. 356/240, 428; 250/223 B; 209/524, 526

[56] References Cited

U.S. PATENT DOCUMENTS 3,107,011 10/1963 Mathias et al. .................. 356/428 X
3,171,033 2/1965 Mathias et al. ............. 250/223 B X
4,391,373 7/1983 Wiggins ........................... 356/240 X

FOREIGN PATENT DOCUMENTS 34348 2/1983 Japan ..................... 356/240

Primary Examiner—Davis L. Willis
Assistant Examiner—Matthew W. Koren

[57] ABSTRACT

A bottle inspecting apparatus comprises means for conveying bottles while rotating the same; a first light source for exposing only the bottle finish with light; a second light source having a radiation spectrum different from that of the first light source for exposing the thread of the bottle neck; a filter for discriminating the light of the first light source scattered at the bottle finish and the light of the second light source scattered at the bottle finish and the thread of bottle neck from the second light source; a first photoelectric transducer for photoelectric array converting the light of the first light scattered at the bottle neck into a first output signal; a second photoelectric transducer for photoelectric array converting the scattered light of the second light source from the bottle finish and the thread of bottle neck into a second output signal; a first defect discriminating circuit for digitalizing the output signal from the first photoelectric transducer and for detecting the defect at the bottle finish; a second defect discriminating circuit for digitalizing the output signal from the second photoelectric transducer and for detecting the defect at the bottle finish and the thread of the bottle neck; and a circuit for judging the quality of bottles for providing a qualification signal in response to the output signals from the first and second defect discriminating circuits.

8 Claims, 7 Drawing Figures

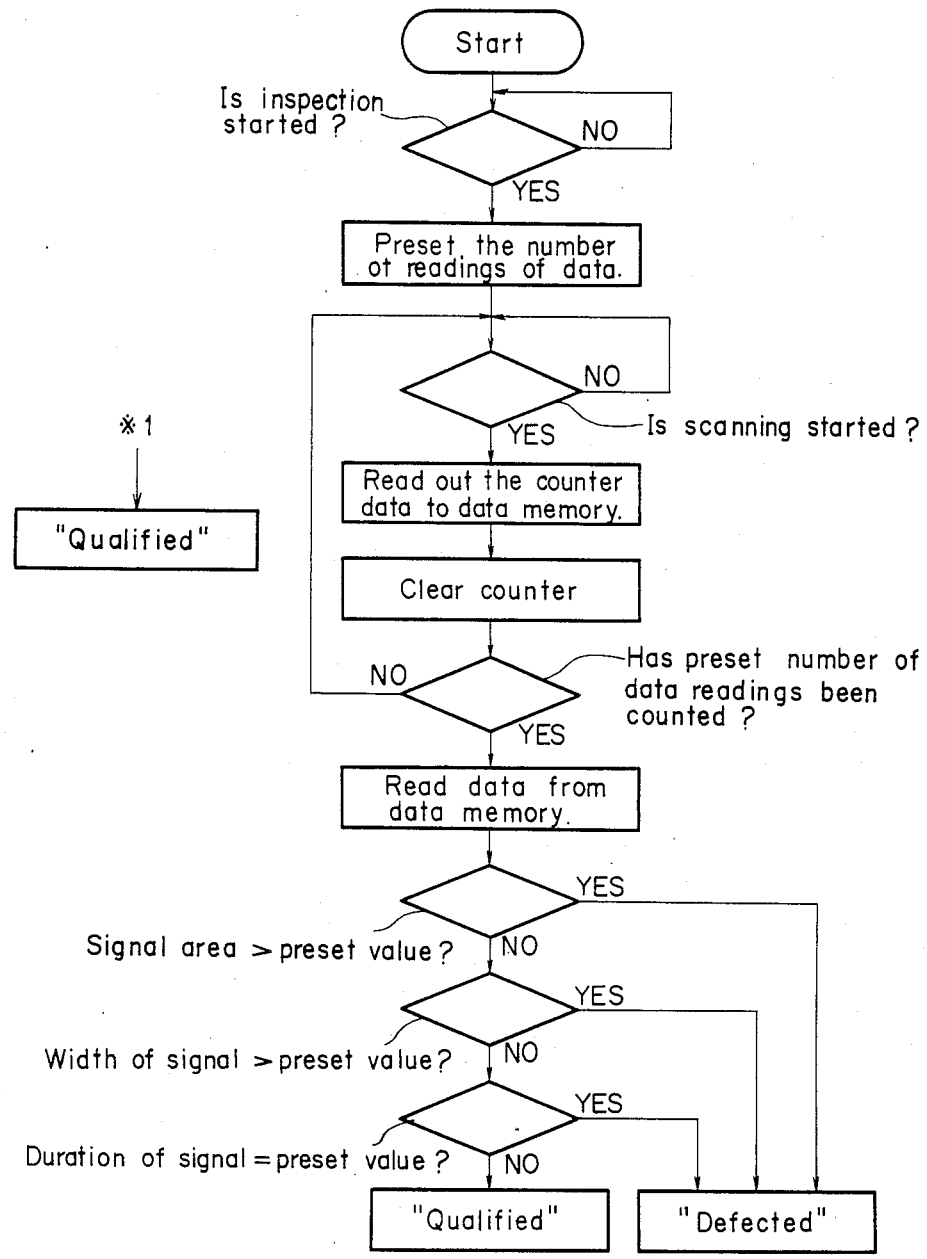

APPARATUS FOR INSPECTING BOTTLES

BACKGROUND OF THE INVENTION

The present invention relates to an apparatus for inspecting bottles, particularly to an apparatus for detecting defects such as a crack, chipping and contamination at the neck and threaded portion thereof of glass bottles which are conveyed on a conveyer.

A conventional bottle inspecting apparatus is disclosed in Japanese Laid Open Patent Application No. 58-34348 entitled "Apparatus for Inspecting Defects of Bottle Neck" filed by the present applicant. As shown in FIG. 1 the disclosed bottle inspecting apparatus mainly comprises bottle conveying means 70 for conveying bottles 1 to be inspected while rotating them; a pair of strip-like light sources 2 along the opposite sides of the conveying means 70 for illuminating the neck 11 and threaded portion thereof 12 of the bottles 1 to be inspected; and light detector means 3 having a field along a diameter line of the bottle neck 11 in alignment with the conveying direction of said conveying means for receiving the light which has been upwardly reflected by the defects and for converting the light into an electric signal.

In the present apparatus, the bottles 1 are conveyed on and along a conveyor 8 while being rotated by means of bottle rotating drive mechanism 7. At this time, the neck 11 and the threaded portion 12 thereof are illuminated by strip-like light sources 2 disposed at the right and left sides of the conveyor 8. Photoelectric transducers 3 comprising photo-diode array 320 are disposed so that they have an elongated field extending in a conveying direction the conveyor 8. The transducers monitor the conveyed and rotating bottle 1 during a half rotation thereof. If there is a defect 1a at the bottle 1 the light is scattered by the defect 1a. A part of the scattered light is directed upward and incident upon the photoelectric transducer 3. After the light is photoelectrically converted the electric signal is converted into digital signal by an analog/digital convertor 4. The digital signal is applied upon the defect detecting circuit 5. However the light may also be scattered by a line of juncture and the begining of the thread (close to the bottle finish of the bottle neck) so that the scattered light may be incident upon the photoelectric transducers 3 disposed above the conveyor 8.

Therefore the signals from the digitalizing circuit 4 include a signal due to defect 1a and a signal due to the line of juncture and the beginning of thread of the bottle 1. The defect discrimination circuit 5 measures the value representative of the area of defective portion and determines the signal exceeding a predetermined value caused by a defect to discriminate the defect 1a from the line of juncture and the beginning of the thread of the bottle.

Since the conventional bottle inspection apparatus has been formed as described above, it fails to find out small defects in the course of the separation between the signal due to defect and the signal due to the line of juncture and the beginning of the thread. The conventional bottle inspection apparatus has a disadvantage in that it does not have enough sensitivity to find the defect at the bottle finish having no line of juncture and the beginning of the thread.

SUMMARY OF THE INVENTION

It is therefore the object of the present invention to provide a novel bottle inspection apparatus.

It is another object of the present invention to provide a bottle inspection apparatus free of the disadvantages of the conventional apparatus.

It is a further object of the present invention to provide a bottle inspection apparatus having an enhanced sensitivity to the defect at the bottle finish.

It is a still further object of the present invention to provide a bottle inspection apparatus which can discriminate between the defect of bottle finish and thread thereof for detecting the defect.

The above mentioned objects of the present invention are accomplished by providing a bottle inspecting apparatus comprising means for conveying bottles while rotating the same; a first light source for exposing only the bottle finish to light; a second light source having a radiation spectrum different from that of the first light source for exposing the bottle finish and the thread of the bottle neck; a filter for discriminating the light of the first light source scattered at the bottle finish and the light of the second light source scattered at the bottle finish and the thread; a first photoelectric transducer for photoelectric array conversion of the light of the first light source scattered at the bottle finish into a first output signal; a second photoelectric transducer for photoelectric array conversion of the scattered light of the second light source from the bottle finish and the thread into a second output signal; a first defect discriminating circuit for digitalizing the output signal from the first photoelectric transducer and for detecting the defect at the bottle finish; a second defect discriminating circuit for digitalizing the output signal from the second photoelectric transducer and for detecting the defect at the bottle finish and the thread; and means for judging the quality of bottles for providing a qualification signal in response to the output signals from the first and second defect discriminating means.

In this apparatus, the filters are disposed between the bottle to be inspected and the first and second photoelectric transducers for directing the light rays which were emitted from the first and second light sources and scattered by the defects at the bottle finish and the thread thereof respectively. The light rays scattered by the defects at the bottle finish and thread thereof are independently measured by the first and second photoelectric transducers respectively for qualifying the bottles. The sensitivity of detection for the defect at the bottle finish of the bottle neck is improved.

BRIEF DESCRIPTION OF THE DRAWINGS

FIG. 7 is a flow chart showing a program which is executed in a microprocessor.

DESCRIPTION OF THE PREFERRED EMBODIMENT

The present invention will be described by way of an embodiment with reference to the drawings.

Figure 1:
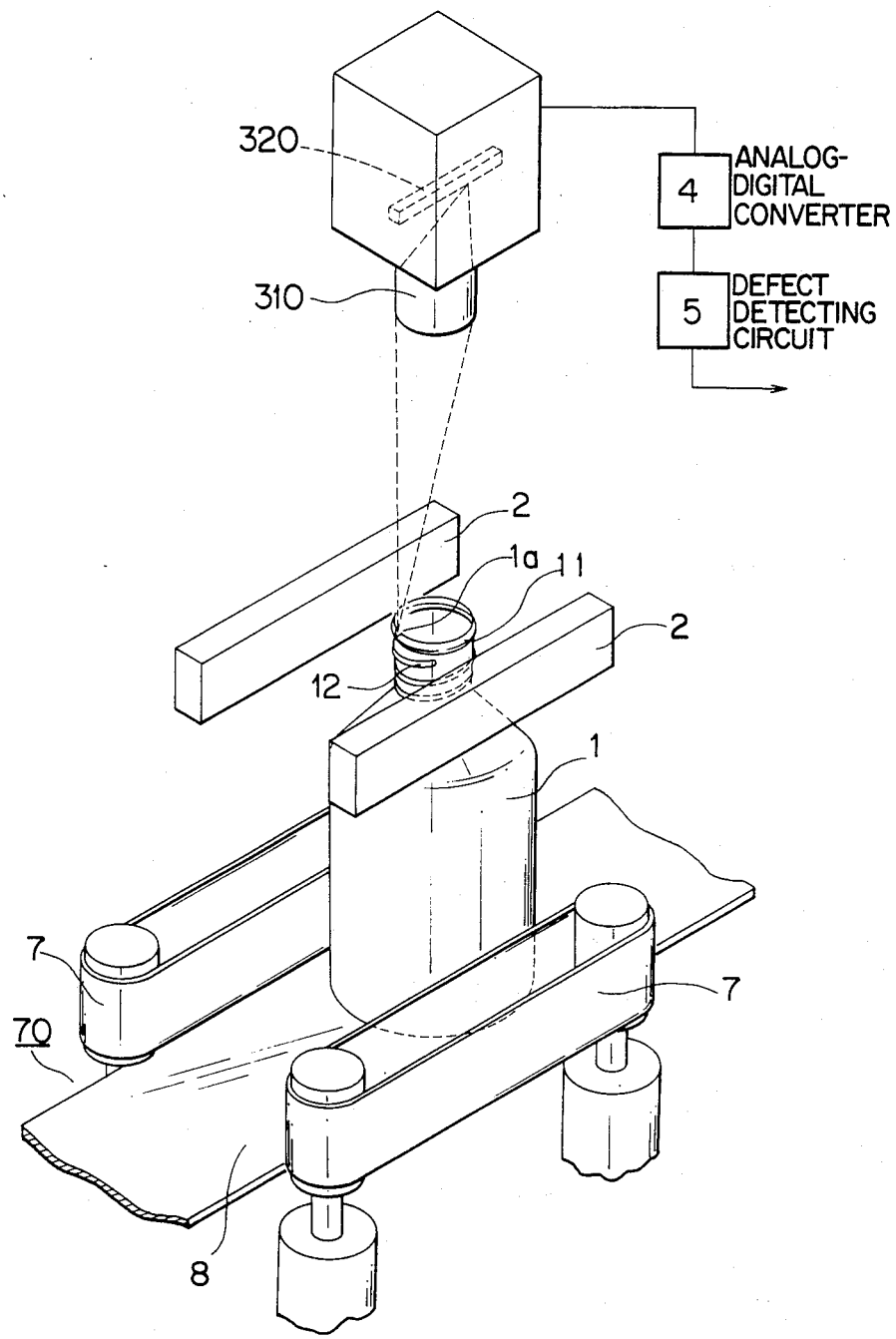
FIG. 1 is a perspective view showing a conventional bottle inspection apparatus.
Figure 2:
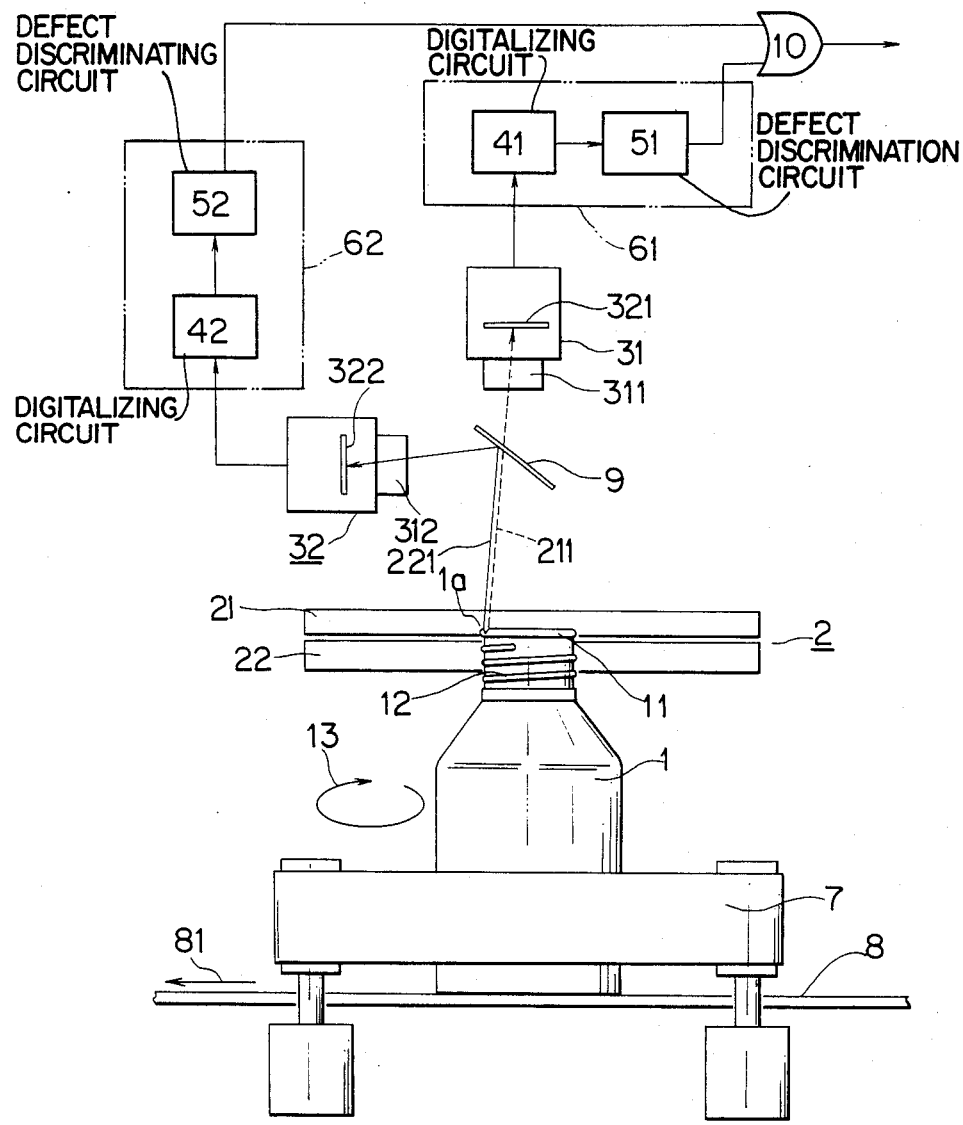
FIG. 2 is a front view and a block diagram showing an embodiment of the bottle inspection apparatus of the present invention.
Figure 3:
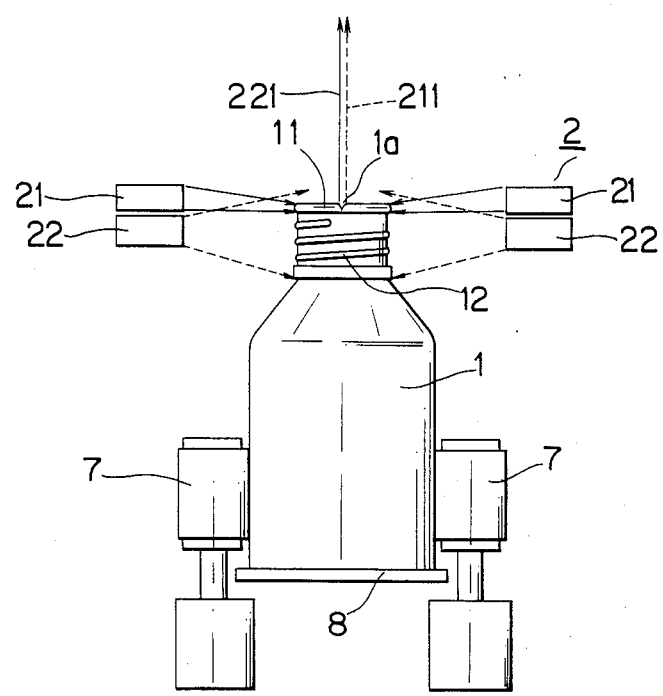
FIG. 3 is a partial front view showing an embodiment of the bottle inspection apparatus of the present invention.

Referring now to FIG. 2, there is shown an embodiment of a bottle inspection apparatus of the present invention. Reference numeral 13 represents the rotational direction of a bottle 1; 21 a first light source for exposing only bottle finish 11 with light; and 22 a second light source having a light emitting spectrum different from that of the first light source 21 for exposing the bottle finish 11 and the thread 12 thereof. The light sources 21 and 22 form a pair of strip-like light sources 2 on both sides of the conveyer 8 to extend in the conveying direction. They face each other with the conveyer 8 therebetween. In FIG. 2 only one of the light sources at the rear of the bottle 1 is shown and the other similar light source in front of the bottle 1 is omitted. The first and second light sources comprise for example a green and a red colour light source respectively. The green light scattered by the defect at the bottle finish 11 travels upward along a light path 211 and the red light scattered by the defects at the bottle finish 11 and the thread 12 thereof travels upward along a light path 221. A filter 9 comprises, for example, a dichroic mirror which transmits the green light, but reflects the red light. The light from the first light source 21 is converted into an electric signal by means of a first photoelectric transducer 31 which comprises a photo-diode array 321 having a self-scanning function. The light from the second light source 22 is converted into an electric signal by means of a second photoelectric transducer 32 which comprises a photodiode array 322 having a self-scanning function. Light collecting lenses 311 and 312 focus the light upon the first and second photoelectric transducers 31 and 32 respectively. First and second defect discriminating means 61 and 62 comprise digitalizing circuits 41 and 42 and defect discriminating circuits 51 and 52 respectively. Reference numeral 81 represents the direction of conveying bottles. Bottle qualification means 10 comprising an OR gate is adapted to generate a bottle qualification signal. FIG. 3 is a partial front view showing an embodiment of the bottle inspection apparatus at an angle different from that of FIG. 2 by 90 degrees.

The operation of the embodiment will be described with reference to FIG. 2.

The bottle 1 which has been conveyed to an inspection zone by the bottle conveyer 8 is moved on and along the conveyer 8 while being rotated by the bottle rotating and driving mechanism 7. At this time, the bottle neck 11 and the threaded portion 12 thereof are illuminated by strip-like light source pair 2 disposed at the both sides of the conveyer 8 as shown in FIG. 3. The strip-like light source pair 2 comprises two light sources, one of which is the first light source 21, a green colour light source which is adapted to illuminate only the bottle finish 11 of the bottle 1 conveyed while being rotated and not to illuminate the thread 12 of the bottle neck. The other light source is the second light source 22, a red colour light source which is adapted to illuminate the bottle finish 11 and the threaded portion 12 of the bottle 1. If there is a defect 1a at the bottle finish 11 of the bottle 1, a part of the light from the first light source 21 which impinges upon the defect is scattered by the defect and is then upwardly directed along the green optical path 211 and transmitted by the dichroic mirror 9 and then focused upon the photodiode array 321 by the light collecting lens 311. The output signal from the first photoelectric transducer 31 is converted to a digital signal having a suitable preset value by the digitalizing circuit 41. The digitalized output signal is applied to the defect discriminating circuit 51. The signal does not include noise signals caused by the line of juncture and the beginning of the thread of the bottle since the field of the photodiode array 321 is taken along the diameter axis of the bottle finish 11 in alignment with the conveying direction of the conveyer 8 and the first light source 21 illuminates only the bottle finish 11. The defect discriminating circuit 51 measures the value corresponding to the area of abnormal portion by counting the output signal of the digitalizing signal and determines that the area exceeds a preset value and simultaneously provides a defect detection signal to the OR circuit 10.

In such a manner the defect 1a at the finish 11 of the bottle 1 is detected by monitoring the bottle finish 11 as a two dimensional image while the bottle 1 is half rotated in the field of photodiode array 321.

The second light source 22 a red light source illuminates the bottle finish 11 and the thread 12 of the bottle. The light which impinges upon the defect at this area is scattered by the defect. Part of the scattered light is upwardly directed and reflected by the dichroic mirror 9 and then focused on the photodiode array 322 by the light collecting lens 312.

The field of the photodiode array 322 is relevant to that of the photodiode array 321 so that they both view the same place. Accordingly the light scattered by the line of juncture and the beginning of the thread of the bottle 1 may be incident upon the photodiode array 322. Thus there is a possibility that the signal which is obtained by digitalizing the output signal from the second photoelectric transducer 32 includes the noise signal caused by the line of juncture and the beginning of the thread of the bottle 1. The defect discriminating circuit 52 which receives the output signal from the digitalizing circuit 42 should remove the noises for detecting the defect. In this case the image of the bottle can be monitored as a two dimensional image by half rotating the bottle 1 within the field of the photodiode array 322. Accordingly three approaches are adopted herein for detecting defect by removing noise.

Figure 4A:
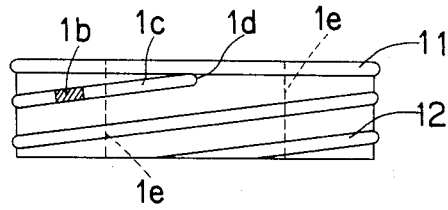
FIGS. 4a and 4b are developed views of the bottle neck and a wave form chart respectively for illustrating a way of defect detection by the second defect detecting means.
Figure 4B:
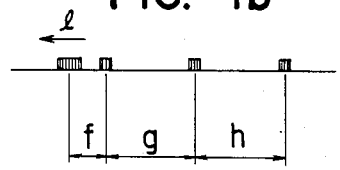

FIGS. 4a and 4b are developed views of the bottle neck and a wave form chart respectively for illustrating the defect detection method of the second defect detecting means of one embodiment of the present invention.

FIG. 4a shows the developed view of the bottle finish 11 and the thread 12 of the bottle. FIG. 4b is a wave form chart showing the output signal from the digitalizing circuit 42. Reference numeral 1b represents a defect such as contamination and the like; 1d the begining of the threaded portion 1c; 1e the line of juncture of bottle 1; f a spacing between the defect 1b and the line of juncture 1e of the bottle 1 and g and h spacings between the beginning of the thread 1d and the line of juncture 1e of the bottle 1; 1 the width of the defect 1b. In accordance with a first approach to detect the defect 1b, the amount relevant to the area of each abnormal portion is measured by adding the output signal of the digitalizing circuit 42 and the amount exceeding a predetermined value is determined as a defect signal. In accordance with a second approach, the signal representative of the abnormal portion having a width 1 in a peripheral direction of bottle neck larger than a preset value is determined as a defect signal on the basis of the scanning of the photodiode array. In accordance with a third approach, one of the abnormal portions is judged as a defect if the reading point of the abnormal portion is shifted from the intervals g and h between the line of juncture of the bottle 1 and the beginning of the thread.

Figure 5:
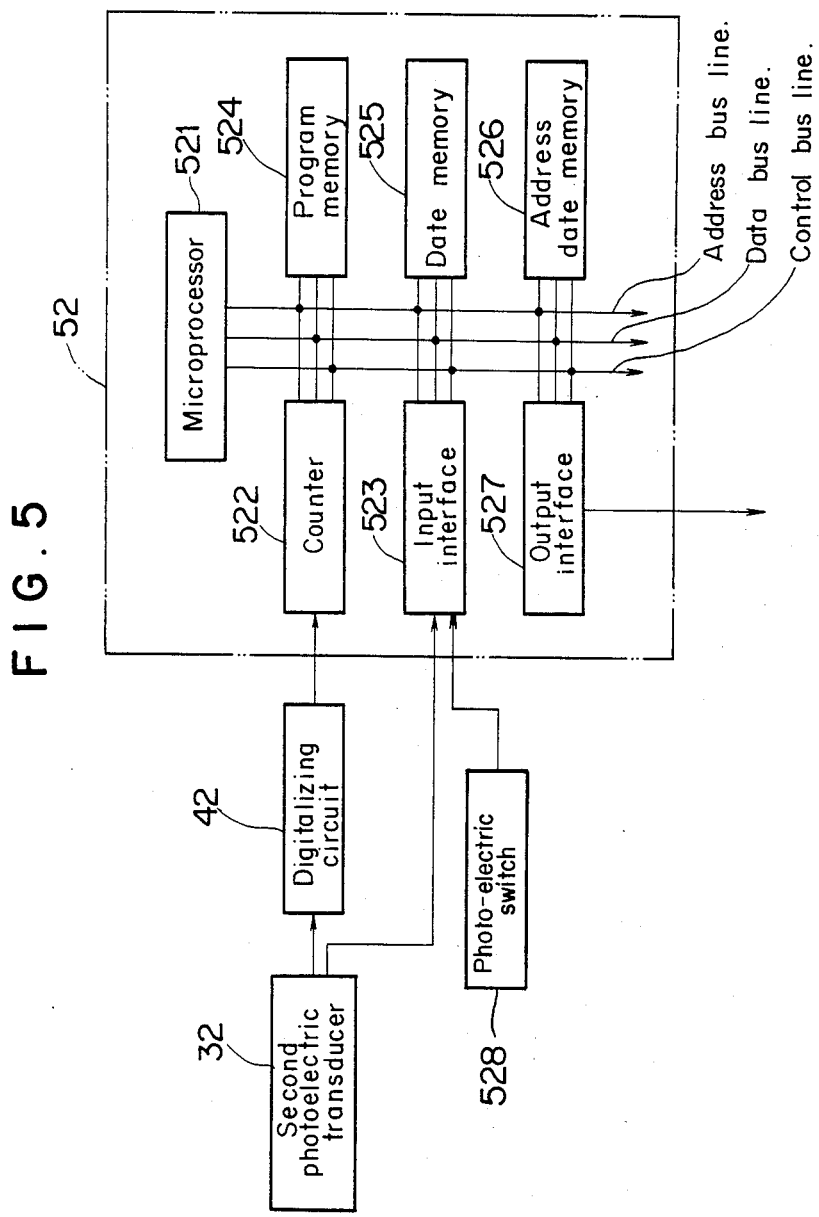
FIG. 5 is a block diagram showing the second defect detecting means.

Referring now to FIG. 5, there is shown one embodiment of a second defect discriminating means of the present invention. Reference numeral 521 represents a microprocessor; 522 a counter; 523 an input interface; 524 a program memory; 525 a data memory; 526 an address data memory; 527 an output interface; and 528 a photoelectric switch. When an inspection initiating signal is applied to the input interface 523 from the photoelectric switch 528, the microprocessor 521 presets the number of data readings relevant to a half rotation of the bottle 1. Whenever a scanning start signal is applied to the input interface 523, the microprocessor 521 reads the data of the counter 522 and resets the same. When the read of data has been executed at the predetermined times, data sampling is finished to begin the judging process. In the judging process, data are sequentially read from data memory. When the data other than zero (abnormal portion) is found, the number of data other than zero is counted and the data are added. In this step, the inspection of the first approach by area and the second approach by width are carried out. That is, a defect is determined when the added values and the counts exceed a predetermined value in accordance with the first and second approaches respectively.

Inspection of third approach by interval is carried out after storing a memory address which is relevant to the middle of the abnormal portion. In other words, the content of the address data memory 526 is inspected. When the interval between the stored addresses is offset from the predetermined value, the presence of defect is determined. In such a manner, defect detection is possible in which the actual defect signal and the noise signal caused by the line of juncture 1e and the beginning of the thread 1d are discriminated. The defect detection signal which is applied to the OR circuit 10 from the defect detection circuit 52 is used as a control signal for rejecting the bottle having the defect. The program shown in FIG. 7 is executed in the microprocessor 521.

Although the light source 2 includes the red and green light sources 22 and 21 having different radiation spectrum in the aforementioned embodiment, other combinations, for example, infrared and visible rays may be used.

Although the filter 9 includes the dichroic mirror 9 which reflects the red light and transmits the green light in the aforementioned embodiment, the dichroic mirror 9 which transmits the red light and reflects green light may be used.

Figure 6:
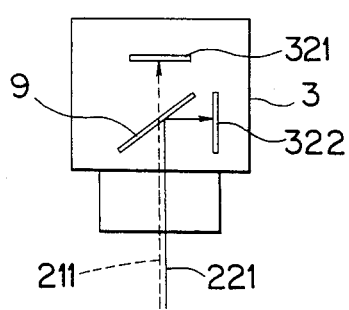
FIG. 6 is a view showing a photoelectric transducer in another embodiment of the present invention.

Although two photoelectric transducers 31 and 32 and the dichroic mirror 9 are used as discrete parts, an integral photoelectric transducer 3 including the dichroic mirror 9 between the light collecting lens 310 and photodiode arrays 321 and 322 may be used as shown in FIG. 6. FIG. 6 shows another embodiment of the photoelectric transducer of the present invention.

Although the red light second source 22 and the green first light source 21 are used as separate lamp houses in the aforementioned embodiment, an integral strip-like light source having a wide range of radiation 1 spectrum including a first and second filters having different light transmitting spectra may be used.

In accordance with the present invention, a highly accurate bottle inspection may be carried out.

What is claimed is:

1. A bottle inspecting apparatus for inspecting bottles having a bottle neck with a bottle finish and a thread, comprising:
   (a) means for conveying bottles while rotating the same;
   (b) a first light source for exposing only the bottle finish to light;
   (c) a second light source having a radiation spectrum different from that of the first light source for exposing the bottle finish and the thread of the bottle neck to light;
   (d) a filter for discriminating between the light of the first light source scattered at the bottle finish and the light of the second light source scattered at the bottle finish and the thread of the bottle neck;
   (e) a first photoelectric transducer having means for photoelectric array conversion of the light of the first light source scattered at the bottle finish into a first output signal;
   (f) a second photoelectric transducer having means for photoelectric array conversion of the light of the second light source scattered from the bottle finish and the thread of bottle neck into a second output signal;
   (g) a first defect discriminating means for digitalizing the first output signal from the first photoelectric transducer and for detecting a defect at the bottle finish;
   (h) a second defect discriminating means for digitalizing the second output signal from the second photoelectric transducer and for detecting a defect at the bottle finish and the thread of the bottle neck; and
   (i) means connected to said first and second discriminating means for judging the quality of bottles for providing a qualification signal in response to the output signals from the first and second defect discriminating means.

2. The bottle inspecting apparatus as defined in claim 1, in which the second defect discriminating means detects the value of the output signal from the second photoelectric transducer which exceeds a predetermined value as a defect.

3. The bottle inspecting apparatus as defined in claim 1, in which the second defect discriminating means counts the output signals from the second photoelectric transducer, which exceed a predetermined value, for detecting a defect when the count exceeds a predetermined count.

4. The bottle inspecting apparatus as defined in claim 1, in which the second defect discriminating means presets the interval of the output signals from the second photoelectric transducer, between the line of juncture of the bottle and the beginning of the thread of a non-defective bottle, and detects a defect when the interval of the output signals exceeding a predetermined value fluctuates from a preset value.

5. The bottle inspecting apparatus as defined in claim 1, in which first and second light sources are provided on each side of the bottle conveying means.

6. The bottle inspecting apparatus as defined in claim 5, in which the first and second light sources each include a strip-like light source having a wide range of light emitting spectra, and a filter having different light transmission spectra.

7. The bottle inspecting apparatus as defined in claim 5, in which the filter reflects the light from the first light source and transmits the light from the second light source.

8. The bottle inspecting apparatus as defined in claim 5, in which the filter transmits the light from the first light source and reflects the light from the second light source.

* * * * *